(12) United States Patent
Boyle et al.

(10) Patent No.: US 7,498,570 B2
(45) Date of Patent: Mar. 3, 2009

(54) ION MOBILITY SPECTROMETER

(75) Inventors: Paul Boyle, London (GB); Andrew Koehl, Cambridge (GB); David Ruiz Alonso, Cambridge (GB)

(73) Assignee: Owistone Ltd., Cambridgeshire (*) Notice: Subject to any disclaimer, the term of this patent is extended or adjusted under 35 U.S.C. 154(b) by 331 days.

(21) Appl. No.: 10/571,871

(22) PCT Filed: Aug. 2, 2005

(86) PCT No.: PCT/GB2005/050126

§ 371 (c)(1), (2), (4) Date: Mar. 15, 2006

(87) PCT Pub. No.: WO2006/046077

PCT Pub. Date: May 4, 2006

(65) Prior Publication Data

US 2008/0054174 A1    Mar. 6, 2008

(30) Foreign Application Priority Data

Aug. 2, 2004 (GB) ................... 0417183.1
Jan. 17, 2005 (GB) ................... 0500840.4

(51) Int. Cl.
*B01D 59/44* (2006.01)
*H01J 49/40* (2006.01)

(52) U.S. Cl. ............ 250/286; 250/287; 250/288; 250/290; 250/282; 250/281; 250/283

(58) Field of Classification Search ............ 250/286, 250/287, 288, 290, 282, 281, 283
See application file for complete search history.

(56) References Cited

U.S. PATENT DOCUMENTS

| | | | |
|---|---|---|---|
| 5,465,480 A | 11/1995 | Karl et al. | |
| 6,107,624 A * | 8/2000 | Doring et al. | 250/286 |
| 6,124,592 A | 9/2000 | Spangler et al. | |

FOREIGN PATENT DOCUMENTS

| | | |
|---|---|---|
| WO | WO 01/35441 | 5/2001 |
| WO | WO 2004/029603 | 4/2004 |

OTHER PUBLICATIONS

Miller et al. "A novel micromachined high-field asymmetric waveform-ion mobility spectrometer" Sensors and Actuators B, vol. 67 (2000) pp. 300 to 306.*

R.A. Miller et al., "A novel micromachined high-field asymmetric waveform-ion mobility spectrometer" Sensors and Actuators B 67 (2000) 300-306.

E.V. Krylov, "Comparison of the planar and coaxial field asymmetrical waveform ion mobility spectrometer (FAIMS)" International Journal of Mass Spectrometry 225 (2003) 39-51.

* cited by examiner

*Primary Examiner*—David A. Vanore
*Assistant Examiner*—Meenakshi S Sahu
(74) *Attorney, Agent, or Firm*—Fish & Richardson P.C.

(57) ABSTRACT

An ion mobility spectrometer is described having an ion filter in the form of multiple parallel ion channels defined by conductive layers separated by non-conductive layers. A time-varying electric potential applied to the conductive layers allows the filter to selectively admit ion species. The device may be used without a drift gas flow. Microfabrication techniques are described for producing microscale spectrometers, as are various uses of the spectrometer.

43 Claims, 13 Drawing Sheets

ION MOBILITY SPECTROMETER

CROSS-REFERENCE TO RELATED APPLICATIONS

This application claims priority under 35 U.S.C. § 371 to PCT/GB2005/050126, filed 2 Aug. 2005, which claims priority to GB0500840.4 filed 17 Jan. 2005 and GB0417183.1, filed 2 Aug. 2004.

FIELD OF THE INVENTION

The present invention relates to an ion mobility spectrometer, and more particularly to a field asymmetric ion mobility (FAIM) spectrometer. Certain aspects of the invention relate to a micro machined FAIM spectrometer. Aspects of the invention also relate to methods of performing ion mobility spectrometry, and to components for use in such a spectrometer.

BACKGROUND TO THE INVENTION

Ion mobility spectrometry is a versatile technique used to detect presence of molecular species in a gas sample. The technique has particular application in detection of explosives, drugs, and chemical agents in a sample, although it is not limited to these applications. Portable detectors are commonly used for security screening, and in the defense industry. However, conventional portable devices are still nonetheless relatively large.

Ion mobility spectrometry relies on the differential movement of different ion species through an electric field to a detector; by appropriate selection of the parameters of the electric field, ions having differing properties will reach the detector at differing times, if at all. Differential mobility of ion species may or may not be exploited. Time of flight (TOF) ion mobility spectrometry measures the time taken by ions when subject to an electric field to travel along a drift tube to a detector against a drift gas flow. By varying the electric field ions of different characteristics will reach the detector differently (if at all), and the composition of a sample can be analysed. This form of spectrometry relies on the length of the drift tube for its resolution; the longer the drift tube, the more powerful the detector. This restricts the possible miniaturisation of such spectrometers, since there is a limit to the lower size of the drift tube which may effectively be used. Further, given that relatively high electric field strengths are necessary, the restriction on drift tube length also results in the need to use relatively high voltages in the device, which may be potentially hazardous to the operator and further restricts the possibility of miniaturisation of the device.

A variation on TOF ion mobility spectrometry is described in U.S. Pat. No. 5,789,745, which makes use of a moving electrical potential to move ions against a drift gas flow towards a detector. A plurality of spaced electrodes are alternately pulsed to generate a moving potential well, which carries selected ions along with it. This device is unsuited to miniaturisation due to, among other reasons, the need for a pump to produce the drift gas flow.

Field asymmetric ion mobility spectrometry (FAIMS) is a derivative of time of flight ion mobility spectrometry (TOFIMS), which potentially offers a smaller form factor; however, existing designs use moving gas flows and high voltages, which are undesirable for microchip implementations. Scaling is further hindered by molecular diffusion, an effect that becomes significant in the micron regime. Background information relating to FAIMs can be found in L. A. Buryakov et al. Int. J. Mass. Spectrom. Ion Process. 128 (1993) 143; and E. V. Krylov et al. Int. J. Mass. Spectrom. Ion Process. 225 (2003) 39-51; hereby incorporated by reference.

Conventional FAIMS operates by drawing air at atmospheric pressure into a reaction region where the constituents of the sample are ionized. Chemical agents in vapour-phase compounds form ion clusters when they are exposed to their parent ions. The mobility of the ion clusters is mainly a function of shape and weight. The ions are blown between two metal electrodes, one with a low-voltage DC bias and the other with a periodic high-voltage pulse waveform, to a detector plate where they collide and a current is registered. Ions are quickly driven toward one electrode during the pulse phase and slowly driven toward the opposite electrode between pulses. Some ions impact an electrode before reaching the detector plate; other ions with the appropriate differential mobility reach the end, making this device a sort of differential mobility ion filter. A plot of the current generated versus DC bias provides a characteristic differential ion mobility spectrum. The intensity of the peaks in the spectrum, which corresponds to the amount of charge, indicates the relative concentration of the agent.

While this arrangement offers the possibility for greater miniaturisation than conventional TOFIMS, the need to generate a gas flow requires the presence of a pump, diaphragm or similar, which using present technology limits the lower size of such a device. Representative examples of such devices are described in U.S. Pat. Nos. 6,495,823 and 6,512,224.

It would be of benefit to provide miniaturised ion mobility spectrometers for use in sensing techniques; not only would these be suitable for covert use or for large scale distribution, the smaller size will allow use of lower voltages in the device. Devices with no or fewer moving parts than conventional devices would also be of benefit, in that they would be more robust than conventional sensors, and so suitable for deployment in high-traffic areas or in harsh environments.

The present inventors have developed a new form of ion mobility spectroscopy in which, broadly speaking, ions are moved back and forth between conducting electrodes and are gradually separated, generally according to their mobility. In embodiments this does not require a drift gas flow for its operation. We will describe how an electric field is used to cause ions to move toward the detector, while a selective tunable ion gate can be used to permit selected ions to reach the detector, and to prevent other ions from doing so. This allows for a solid state construction which does not require a gas pump or similar, so allowing for greater miniaturisation of the device than would otherwise be possible, as well as a more robust construction. In addition, the tunable ion gates may be used in combination with other spectrometers, such as those which use a drift gas flow. Devices of this type are suitable for miniaturisation.

The system as a whole can be reduced in size and cost, since no pump is necessary and the electronics may be reduced in size. Size reduction permits smaller gap sizes between electrodes and hence lower voltages, leading to smaller, more integrated electronics, more precise and controllable waveforms, and improved performance in terms of power usage and resolution. The spectrum of detected ions can provide information on multiple analytes simultaneously, since the ion filter is readily retunable simply by altering the electric field properties. Detection of additional analytes may be incorporated by altering the software controlling the filter and subsequent analysis, so making the system highly customisable.

Other advantages of the present invention include the reduction of false positives by adjustment of multiple parameters over time, which again may be achieved with software control. Many detectors may be networked together to combine outputs, to reduce the deleterious effects of local interferents and increase classification confidence, as well as to make the system as a whole more robust.

Finally, the present invention is highly sensitive, allowing detection at trace levels, and rapid. With a reduced distance between ioniser and detector the time for which ions must exist to be detected is reduced, so allowing detection of short-lived ions. The system may be operated at low voltages, and at low power, allowing for longer operational use in a range of environments.

SUMMARY OF THE INVENTION

According to a first aspect of the present invention, there is provided an ion mobility spectrometer comprising an ionizer, an ion filter, and an ion detector;

wherein the ion filter defines at least one ion channel along which ions may pass from the ionizer to the ion detector; and wherein the ion channel is defined by a plurality of conductive layers separated along the length of the channel by at least one non-conductive layer;

the spectrometer further comprising control means for applying electric potential to the conductive layers of the ion channel.

By application of electric potential to the conductive layers, an electric field may be established within the ion channel. This electric field will affect the mobility of ions within the channel according to the nature of the field and the charge of the ions, and so can be used to selectively admit ions through the channel to the detector. The use of such a tunable filter means that a long drift tube is not necessary to filter the ions.

The spectrometer may further comprise a deflector, for deflecting ions away from the ionizer and towards the ion detector. This may be achieved by use of a deflector electrode and by establishing an electric field gradient between the deflector electrode and the ion detector. Such an arrangement permits ions to be driven through the filter and towards the detector without the use of a drift gas flow (although the spectrometer may be used in combination with a drift gas flow in some circumstances). Spectrometers according to the invention may therefore be made with fewer moving parts than conventional spectrometers.

Preferably the control means allows the application of a time-varying electric potential to the conductive layers. The electric potential may be oscillating, and is conveniently in the form of a square wave. The electric potential may be time-varying in an asymmetric manner.

The control means preferably allows the electric potential to be selectively varied; this allows for the field to be tuned in order to permit detection of particular ions.

The ionizer may comprise any convenient means; for example, a source of ionising radiation, a UV source, or the like.

The filter preferably comprises a plurality of ion channels, and conveniently more than 5, more than 10, more than 15, and more than 20 ion channels. The channels may conveniently be defined by a plurality of electrode fingers forming a comb-like arrangement. In preferred embodiments, the filter comprises two or more interdigitated electrode arrays, each array having a plurality of electrode fingers. The presence of multiple ion channels permits a relatively large ionisation volume to be used adjacent the channels, thereby improving sensitivity of the spectrometer compared with conventional devices having a single ion channel and hence restricted to a relatively small ionisation volume.

Preferably the ion channels are elongate; that is, they have a relatively short length (the direction along which ions will flow) and a relatively short width (in a minor transverse direction), with a relatively long depth (in a major transverse direction).

Optionally the interdigitated fingers may be curved, more particularly serpentine, and in this way may then define curved or serpentine channels. This has the advantage of reducing diffusion losses which, with straight electrodes, are caused by ions diffusing into the walls of the channels. With curved or serpentine electrodes these diffusion losses are reduced (and the channel width in this sense is effectively increased) because of the formation of a partial potential well within a channel.

Thus in another aspect the invention provides an ion filter having channels defined by electrodes with this general formation. Also provided is an ion filter comprising two interdigitated electrodes forming a plurality of ion channels. Such an arrangement may be used as described, or with a drift gas flow; the smaller gap size provided by the interdigitated filter arrangement still provides advantages of reduced voltages and hence simpler control electronics even when a drift gas flow is used.

The filter may comprise a resistive or semiconductive substrate on which the conductive layers and non-conductive layer are provided. The substrate may in certain embodiments be the ion detector, while in other embodiments a distinct substrate may be provided. The substrate and/or the non-conductive layer may comprise silicon, conveniently in the form of silicon dioxide or silicon nitride. The substrate may be in the form of a silicon wafer. The conductive layers may comprise doped polysilicon. In preferred embodiments, where the spectrometer is on a micro machined scale, the conductive and non-conductive layers (and optionally the substrate, if a separate substrate is provided) may conveniently be etched to form a desired shape and configuration, and to provide the ion channels, using conventional semiconductor processing techniques. This allows many channels to be formed in parallel, and on a small scale.

Preferably the length of the ion channel is less than the depth of the filter, and preferably significantly less; for example, at least 10 times less. In preferred embodiments, the filter has a generally wafer-like form, with the channel length being a fraction of the filter depth. In a particularly preferred embodiment, the channel length is less than 1000 microns, less than 900 microns, and less than 800 microns, while the filter width is more than 10,000 microns. Preferred channel lengths are from 1000 to 100 microns, more preferably 800 to 300 microns, and most preferably 500 to 300 microns.

Preferably also the width of the ion channel (that is, the gap spacing across the channel over which the transverse electric field is generated) is less than the channel length. In preferred embodiments the gap spacing is between 10 and 100 microns. Such an arrangement allows the generation of relatively large electric fields across the channel length with relatively low voltages and power consumption. In preferred embodiments of the invention, the electric fields may be large enough to cause ion fragmentation or ion cracking. This allows large ion species to be fragmented into smaller species, which can improve detector sensitivity and reduce the likelihood of interferents obscuring results.

Conveniently at least two, and preferably two, conductive layers are provided. A plurality of non-conductive layers are conveniently provided, and preferably two. The conductive layers may alternate with non-conductive layers (that is, a non-conductive layer is interposed between each pair of conductive layers); in a preferred embodiment, the filter has the structure C-NC-C-NC-(and optionally, a substrate), where C and NC represent conductive and non-conductive layers respectively. This embodiment is suited for use where the substrate is also the ion detector.

In an alternative preferred embodiment, the filter has the structure C-NC-substrate-NC-C; that is, the substrate carries a non-conductive layer on both faces with a conductive layer above the non-conductive layer. This embodiment is particularly suited for use where a distinct substrate is provided.

The spectrometer preferably comprises means for heating the filter. Preferably the filter may be heated to at least 150° C. Heating the filter can improve performance, and will assist in removing contaminants from the filter. A separate heater may be provided (for example, a substrate on which the filter is mounted), although preferably the heating means is integrated with the filter. In preferred embodiments, the filter comprises a substrate which is heated, for example by Joule effect heating when a voltage is applied across the substrate. If the substrate is integrated into the filter, then such a voltage will be applied when the filter electrodes are actuated. The preferred microscale embodiments of the invention allow relatively low voltages to be used to provide effective heating by the Joule effect.

The spectrometer conveniently comprises a plurality of functional layers; each layer may have a wafer-like form. This arrangement is advantageous in assembling a micro machined spectrometer since it allows mass production (such as batch or parallel manufacturing) semiconductor techniques to be used. The use of semiconductor techniques generally means that manufacture will take place in a clean room environment, such that lengthy decontamination and preparation steps are not needed before the assembled product can be used.

Such a spectrometer will also be relatively compact due to the layer structure, which thus allows for greater miniaturisation than otherwise. For example, each of the ionizer, filter, and detector may comprise a functional layer. In certain embodiments, it is possible to combine one or more functional layers on a single physical wafer-like layer. For instance, the filter layer and detector layer could be merged by using a silicon on insulator (SOI) wafer handle layer as the detector electrode and depositing the integrated circuitry on the backside, or simply moving the control electronics out of the device. The ionizer could be integrated with an inlet layer by patterning a metallic radioisotope film on the underside of the inlet slab. In one embodiment, the sensor could be composed of just two layers: an integrated filter and detector layer fabricated in a single SOI wafer, and a porous inlet cap with metal ionization material patterned on the underside. This embodiment would require just one bonding step.

In embodiments the channels are substantially perpendicular to a face of the filter. Preferably the filter has face area to channel length ratio of greater than 1:1 (mm), more preferably greater than 10:1 or 100:1 (millimeters). For example a filter may have an 8 mm×8 mm face area and a channel length of approximately 200 µm.

The spectrometer may further comprise one or more of the following additional components; in preferred embodiments, each of these forms an additional functional layer:

a) An inlet layer may be present, to prevent unwanted particles from entering the spectrometer while permitting analytes to diffuse into the device. The inlet layer is conveniently made from a porous material, such as a porous ceramic.

b) A dehumidifier layer to deplete water vapour from the spectrometer. This layer may comprise an absorbent material; alternatively a desiccant or similar may be used. The layer may further include a heating element, which may be used to purge the absorbent material periodically.

c) A preconcentrator layer, to accumulate and periodically release analyte to effectively concentrate the analyte. This layer may also comprise an absorbent material, such as a molecular sieve having pores of an appropriately large size to absorb the desired range of analytes. A heating element may then be activated to release absorbed analytes periodically.

d) A dopant layer comprising a material impregnated with a desired chemical or dopant that is released or desorbed from the layer and into the active region to affect chemical reactions and therefore modify performance. This could be for example ammonia to enhance atmospheric pressure ionization of certain compounds or could be for example water, which is known to enhance separation of compounds in the spectrum and therefore resolution.

The detector may comprise an electrode located on a substrate. Conveniently the detector is a wafer-like semiconductor substrate; for example, silicon. The detector may further comprise control circuitry and the like; this is conveniently formed on the semiconductor substrate. The detector may further comprise connectors for connecting the control circuitry and/or the electrode to a processor means or the like for monitoring the electrode or controlling the device.

The spectrometer may also comprise means for generating a gas counterflow through the filter against the direction of movement of ions. Rarely will all of a sample be ionised, such that intact molecules or partial ionisation products may enter the filter. Such molecules may be reactive, either with the filter itself or with the ionised sample, and so obscure the detected ions. The use of a gas counterflow can assist in removing contaminants from the filter, or in maintaining an unreactive environment within the filter. The gas used may be unreactive—for example, nitrogen or helium—or may be selected to affect affinity of contaminants to ionisation—for example, acetone may be used. A gas counterflow can also be used to alter mobility of ions within the filter. The gas counterflow may be at a very low flow rate; for example, a minimal pressure difference between sides of the filter is generally sufficient, since the flow is not needed to move ions (unlike gas flows in conventional ion spectrometers). Thus miniaturised pumps or diaphragms may be used, with relatively low power consumption; or a pressurised gas reservoir may be used.

According to a further aspect of the invention, there is provided a method of analysing a sample, the method comprising the steps of:

ionising a sample to generate ions adjacent an ion channel, the ion channel being defined by a plurality of conductive layers separated along the length of the channel by at least one non-conductive layer;

biasing the ions such that, in the absence of other forces, they would tend to travel along the ion channel;

applying electric potential to the conductive layers, such that an electric field is established within the ion channel; and detecting generated ions which have passed through the ion channel.

Preferably the ions are biased by application of a longitudinal electric field along the length of the channel.

The electric potential applied to the conductive layers is preferably a time-varying electric potential. The electric potential may be oscillating, and is conveniently in the form of a square wave. The electric potential may be time-varying in an asymmetric manner.

The method may further comprise the step of selectively varying the electric potential; this allows for the field to be tuned in order to permit detection of particular ions.

The ion channel is preferably defined along its length by conductive layers alternating with non-conductive layers (that is, a non-conductive layer is interposed between each pair of conductive layers); in a preferred embodiment, the layers have the structure C-NC-C-NC, where C and NC represent conductive and non-conductive layers respectively. In an alternative preferred embodiment, the layers have the structure C-NC-substrate-NC-C; that is, a substrate carries a non-conductive layer on both faces with a conductive layer above the non-conductive layer.

The method may also comprise the step of applying a counterflow of gas across the filter opposed to the direction of motion of the ions.

The method may further comprise the step of fragmenting ions by application of a sufficiently large electric field across the ion channel.

The ion channel may be heated, for example by applying sufficient voltage across a substrate to generate Joule heating.

According to a further aspect of the present invention, there is provided an ion filter for use in an ion mobility spectrometer, the filter defining at least one ion channel along which ions may pass, wherein the ion channel is defined by a plurality of conductive layers separated along the length of the channel by at least one non-conductive layer.

The filter preferably comprises a plurality of ion channels, and conveniently more than 5, more than 10, more than 15, and more than 20 ion channels. The channels may conveniently be defined by a plurality of electrode fingers forming a comb-like arrangement. In preferred embodiments, the filter comprises two or more interdigitated electrode arrays, each array having a plurality of electrode fingers, optionally curved as previously described.

The channels may conveniently be defined (at least at either end) by a plurality of electrodes with apertures, for example slots.

The filter may comprise a resistive or semiconductive substrate on which the conductive layers and non-conductive layer are provided. The substrate may in certain embodiments be the ion detector, while in other embodiments a distinct substrate may be provided. The substrate and/or the non-conductive layer may comprise silicon, conveniently in the form of silicon dioxide or silicon nitride. The substrate may be in the form of a silicon wafer. The conductive layers may comprise doped polysilicon. In preferred embodiments, where the spectrometer is on a micro machined scale, the conductive and non-conductive layers (and optionally the substrate, if a separate substrate is provided) may conveniently be etched to form a desired shape and configuration, and to provide the ion channels, using conventional semiconductor processing techniques. This allows many channels to be formed in parallel, and on a small scale.

Preferably the length of the ion channel is less than the depth of the filter, and preferably significantly less; for example, at least 10 times less. In preferred embodiments, the filter has a generally wafer-like form, with the channel length being a fraction of the filter depth. In a particularly preferred embodiment, the channel length is less than 1000 microns, less than 900 microns, and less than 800 microns, while the filter width is more than 10,000 microns. Preferred channel lengths are from 1000 to 100 microns, more preferably 800 to 300 microns, and most preferably 500 to 300 microns.

Preferably the ion channels are elongate; that is, they have a relatively short length (the direction along which ions will flow) and a relatively short width (in a minor transverse direction), with a relatively long depth (in a major transverse direction).

Conveniently at least two, and preferably two, conductive layers are provided. A plurality of non-conductive layers are conveniently provided, and preferably two. The conductive layers may alternate with non-conductive layers (that is, a non-conductive layer is interposed between each pair of conductive layers); in a preferred embodiment, the filter has the structure C-NC-C-NC-(and optionally, a substrate), where C and NC represent conductive and non-conductive layers respectively. This embodiment is suited for use where the substrate is also the ion detector.

In an alternative preferred embodiment, the filter has the structure C-NC-substrate-NC-C; that is, the substrate carries a non-conductive layer on both faces with a conductive layer above the non-conductive layer. This embodiment is particularly suited for use where a distinct substrate is provided.

According to a still further aspect of the present invention, there is provided a method of manufacturing an ion mobility spectrometer, the method comprising the steps of:

providing a generally planar resistive preferably insulating substrate having thereon a plurality of conductive layers separated by at least one non-conductive layer;

patterning, for example etching the substrate to provide a filter comprising two or more interdigitated electrode arrays defining a plurality of ion channels themselves defined by a plurality of conductive layers separated along the length of the channel by at least one non-conductive layer; and attaching, for example bonding said filter on one face to a generally planar ionisation layer comprising means for ionising an analyte.

The method may further comprise the step of bonding said filter on an opposed face to a generally planar ion detector layer comprising a detector electrode; in certain embodiments however this detector layer may be formed by the substrate.

BRIEF DESCRIPTION OF THE DRAWINGS

These and other aspects of the present invention will now be described by way of example only with reference to the accompanying Figures, in which.

DETAILED DESCRIPTION OF THE DRAWINGS

Figure 1:
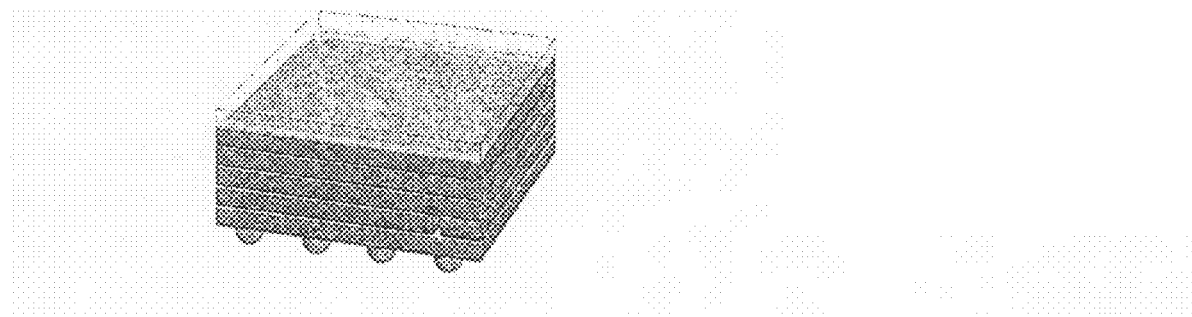
FIG. 1 is a perspective view of a spectrometer in accordance with an embodiment of the present invention.

FIG. 1 shows a perspective view of one embodiment of the sensor of the present invention. The sensor is formed from a number of separate layers bonded together. The ion channels are oriented vertically so that ion movement is directed perpendicular to the silicon substrate surface. This geometry permits subsystems to be segregated to separate wafer layers that are stacked and bonded in the order of ion flow, producing a fully integrated gas sensor with the smallest possible size.

Figure 2:
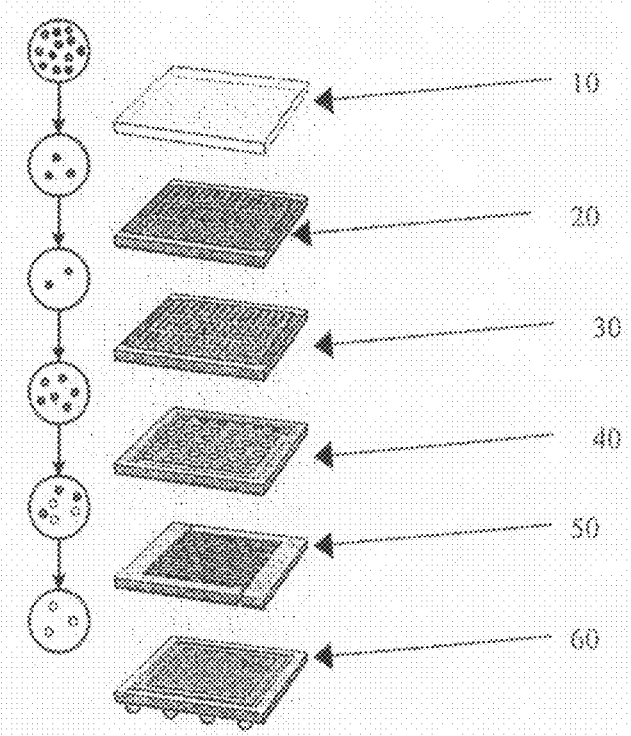
FIG. 2 is an exploded perspective view of the spectrometer of FIG. 1.

An exploded perspective view of the sensor is shown in FIG. 2. The spectrometer includes a number of layers. From top to bottom, these layers are: an inlet layer 10 (a porous ceramic which allows entry of analytes to the sensor), dehumidifier layer 20 (which removes water vapour from the sample), preconcentrator layer 30 (which concentrates the admitted analyte), ionizer layer 40 (in the form of a radioactive substance deposited onto a substrate), filter layer 50, and detector layer 60 (comprising an electrode and electrical connections to a data processor).

This is only one embodiment envisioned and could be greatly simplified in a variety of ways. For instance, the filter layer and detector layer could be merged by using the silicon on insulator (SOI) wafer handle layer as the detector electrode and depositing the integrated circuitry on the backside, or simply moving the control electronics out of the device. The dehumidifier and preconcentrator layers could be integrated together on the same layer, or moved outside of the device and into the cavity housing the sensor. The ionizer could be integrated with the inlet layer by patterning a metallic radioisotope film on the underside of the inlet slab. In one embodiment, the sensor could be composed of just two layers: an integrated filter and detector layer fabricated in a single SOI wafer, and a porous inlet cap with metal ionization material patterned on the underside. This embodiment would require just one bonding step.

Our concept excels by harnessing small size properties for improved performance. The microstructured filter layer uses low voltages and implements a novel method of analyte transport, which eliminates the need for moving gas flows and allows pumpless operation. Microscale thermal isolation facilitates low power operation of a fast microscale preconcentrator. A closely integrated detector improves sensitivity. The small size of the sensor cavity allows a simple approach for removing performance degrading humidity. The batch fabrication advantages of our micro-electro-mechanical-system (MEMS) implementation make it well suited for ubiquitous deployment scenarios.

Figure 3:
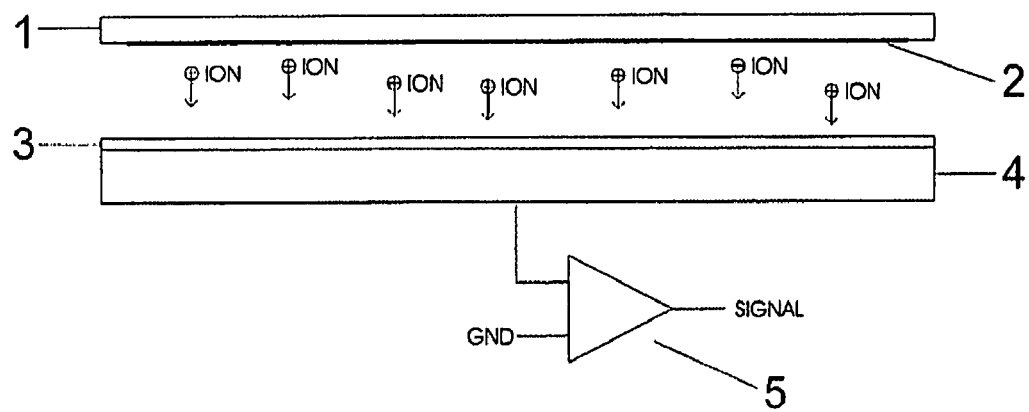
FIG. 3 is a schematic diagram of one embodiment of a spectrometer in accordance with the present invention.
Figure 4:
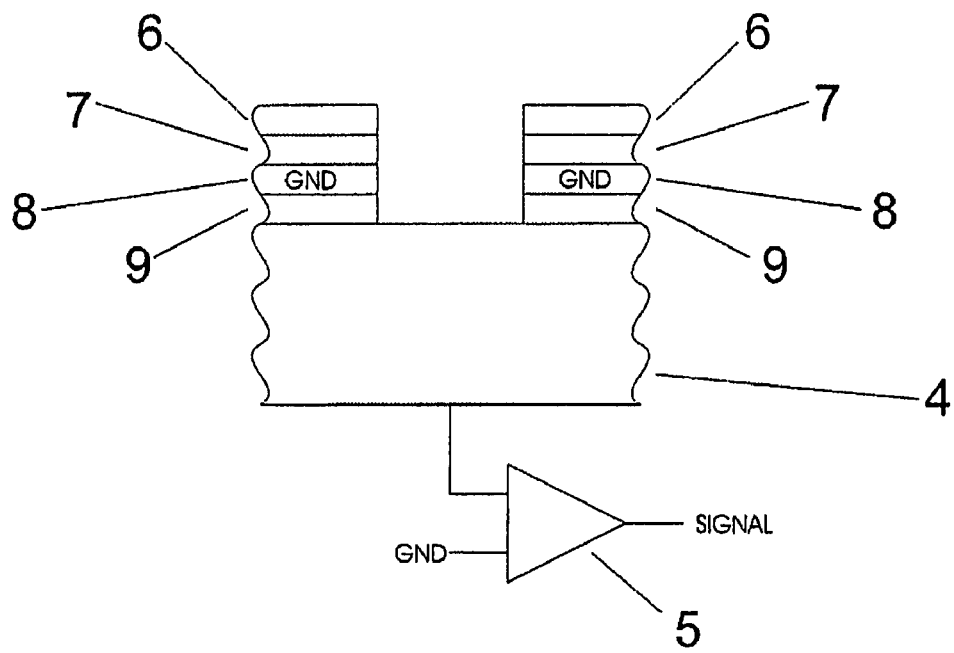
FIG. 4 shows the filter structure of the spectrometer of FIG. 3.

FIGS. 3, 4, and 5 illustrate one preferred embodiment of a spectrometer in accordance with the present invention. The spectrometer consists of an ionization source 2, a deflector electrode 1, a collector electrode 4, a current amplifier 5, and a tunable ion filter structure 3, as shown in FIG. 3. The ionization source 2 is formed on the surface of the deflector electrode 1, while the ion filter structure 3 is formed on the surface of the collector electrode 4, which acts as a substrate to the filter structure. The deflector electrode is held at a positive or negative voltage bias with respect to the collector electrode, so that ions created by the ionization source between the two are driven towards one of the electrodes. Ions directed towards the collector are selectively admitted to the electrode by the tunable ion filter structure. Ions admitted to the collector are neutralized at the electrode surface and transfer their charge to the current amplifier, to produce an amplified signal for output. By tuning the filter structure, ions are permitted to pass depending on characteristic mobility value and are subsequently detected by the amplifier to produce an ion mobility spectrum signal.

The construction of the ion filter structure is shown in FIG. 4. In one embodiment, the structure consists of two conductive layers 6, 8 sandwiched between two insulative layers 7, 9. The lower conductive layer acts as a guard electrode and is held at ground potential to prevent leakage currents from flowing between the top conductive layer and the collector electrode 4, as the signal detected by the current amplifier is typically on the order of picoamperes or less. All layers may be on the order of several hundred nanometers thick. The conductive layers may be made of doped polysilicon, the insulative layers may be made of silicon dioxide or silicon nitride. The collector electrode may be made of doped silicon. The layers are etched away to form the channel structure shown in FIG. 2 (see filter layer 50). Conventional semiconductor processing techniques may be used to form many thousands of channels in parallel.

The filter structure can be manufactured by a range of conventional microfabrication techniques. One representative process involves the following steps. The substrate used is a high resistivity silicon wafer. Aluminium is deposited on the top and bottom faces of the wafer, followed by a photo resistant coating on each face. The top face is masked and subjected to photolithography, after which the aluminium coating of the top face is wet etched to provide an array of electrodes. The photoresist is stripped from both faces, and the process repeated to form the bottom face electrodes. A further resist coating is applied to the top face, after which the silicon is etched from the lower face using deep reactive ion etching to form channels. The photoresist is stripped for the final time, and the filter is ready for further processing.

In a variation of this technique, the silicon wafer may be initially bonded on the bottom face to a glass substrate; the various etching steps are then carried out from the top face to create channels and electrodes, after which the glass substrate is acid etched to expose the bottom face of the wafer, leaving a glass support in contact with the wafer. Other variations may include the use of substrates other than glass; and performing the steps listed in a different order.

Figure 11:
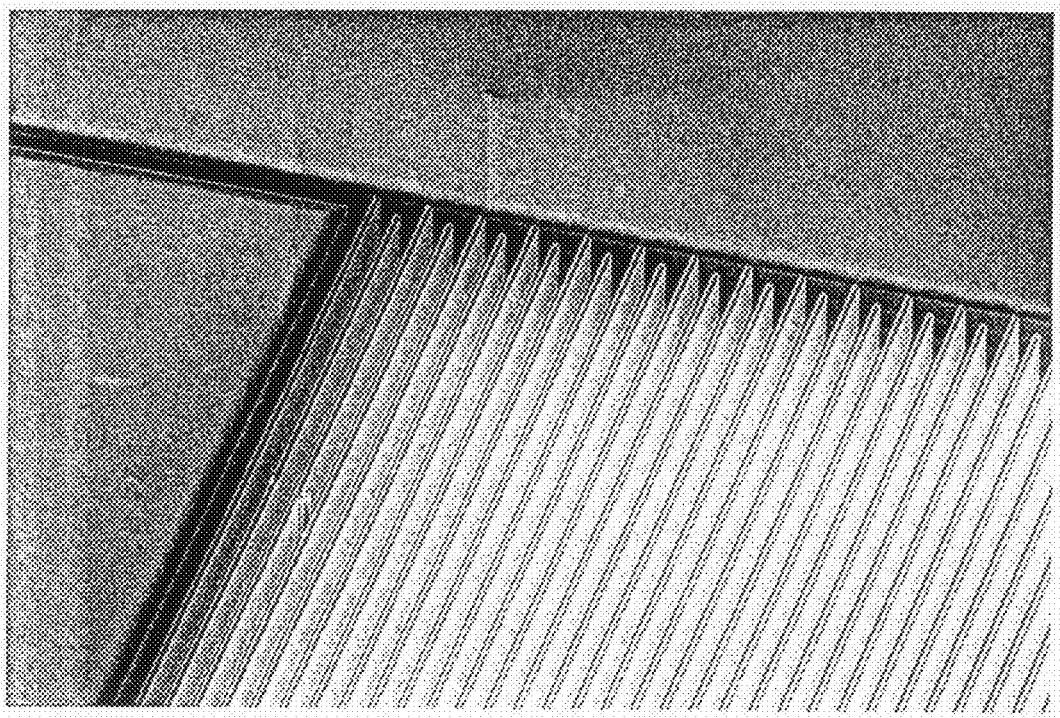
FIG. 11 is an electron micrograph of a portion of an ion filter in accordance with an embodiment of the present invention, illustrating the filter structure.

FIG. 11 shows an electron micrograph of a portion of a filter structure of the present invention.

Figure 5A:
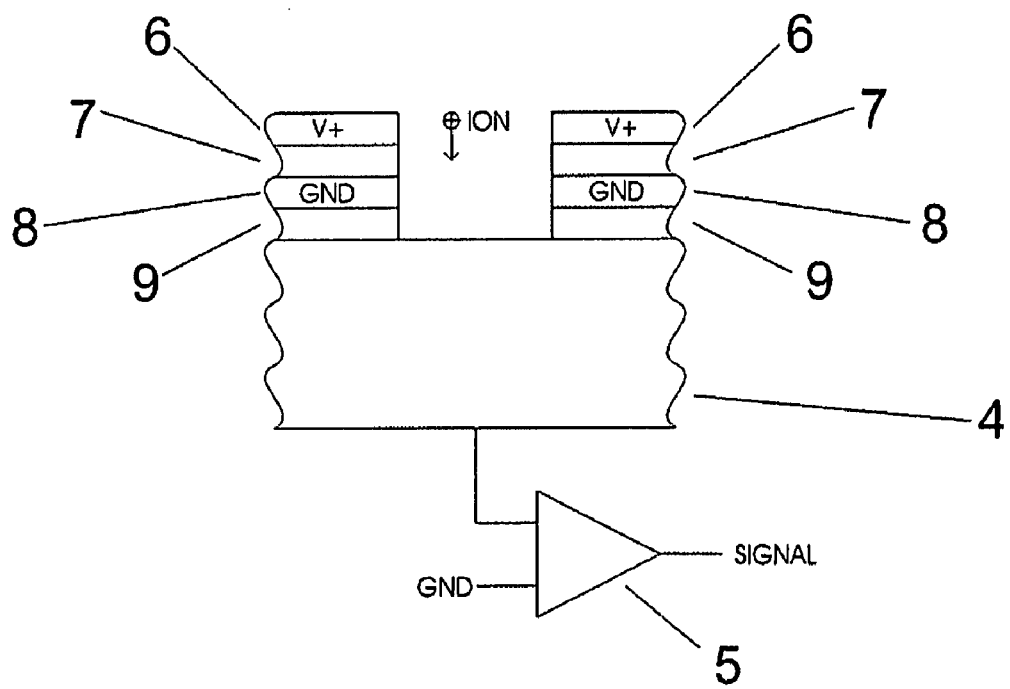
FIGS. 5a and 5b illustrate the operation of the filter structure of FIG. 4.
Figure 5B:
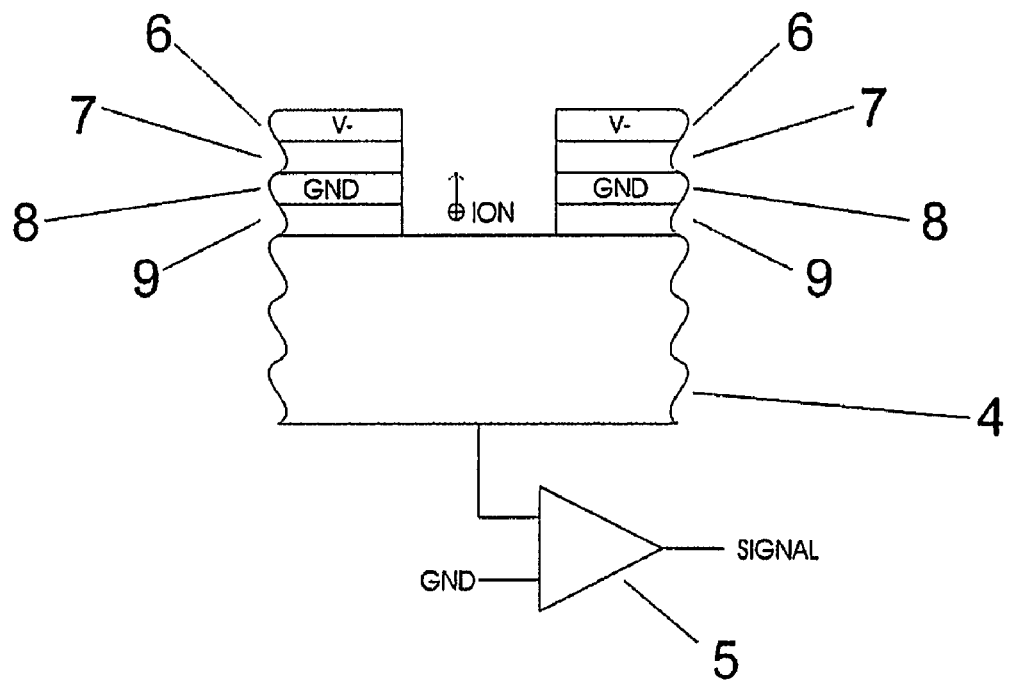
Figure 10:
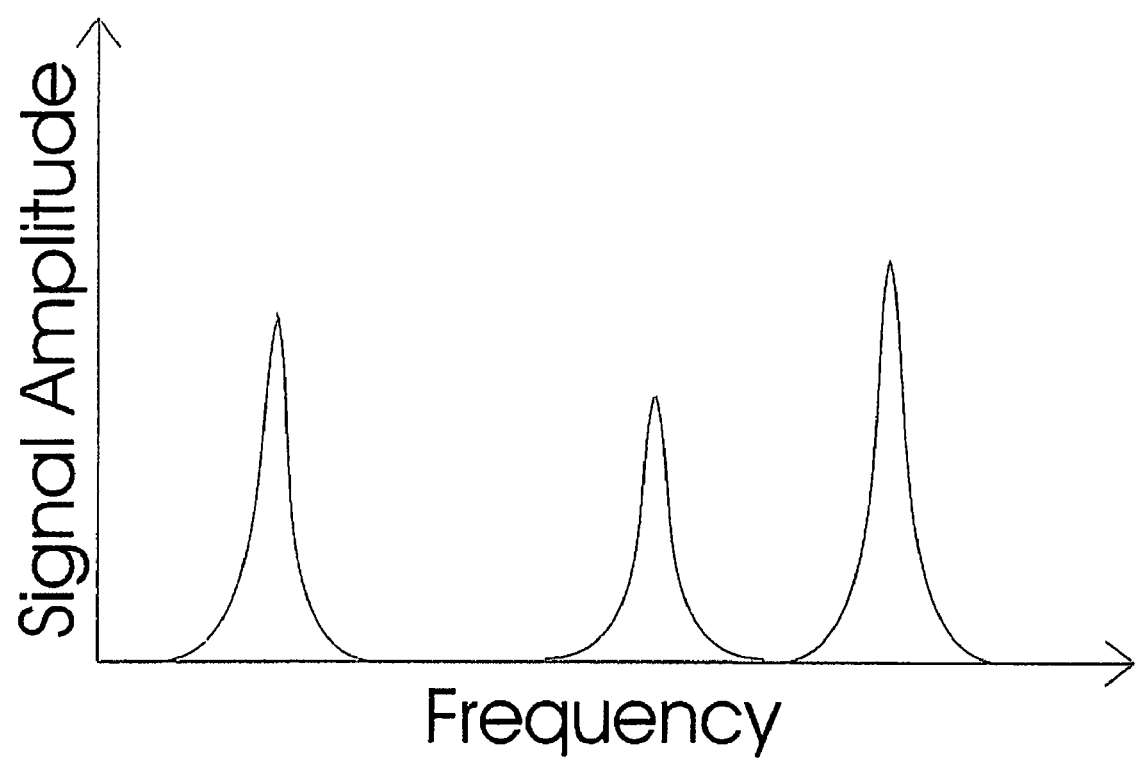
FIG. 10 is a schematic illustration of a sample output of a spectrometer in accordance with the present invention.

The action of the filter structure is depicted in FIG. 5. An oscillating waveform is applied to the top conductive layer 6 so that its potential is oscillated positive and negative with respect to the collector electrode potential seen through the current amplifier (ground). Ions directed into the channel region by the deflector electrode are alternately driven towards the collector FIG. 5a and then away from the collector FIG. 5b depending on the phase of the waveform. Ions with high enough velocities, and hence large mobility values, reach the collector electrode between the phases. Ions with velocities that are too slow, and hence mobility values too small, do not reach the collector. An ion mobility spectrum like that shown in FIG. 10 of the ambient gas is formed by scanning the frequency of the waveform and differentiating the signal output by the current amplifier.

Figure 6:
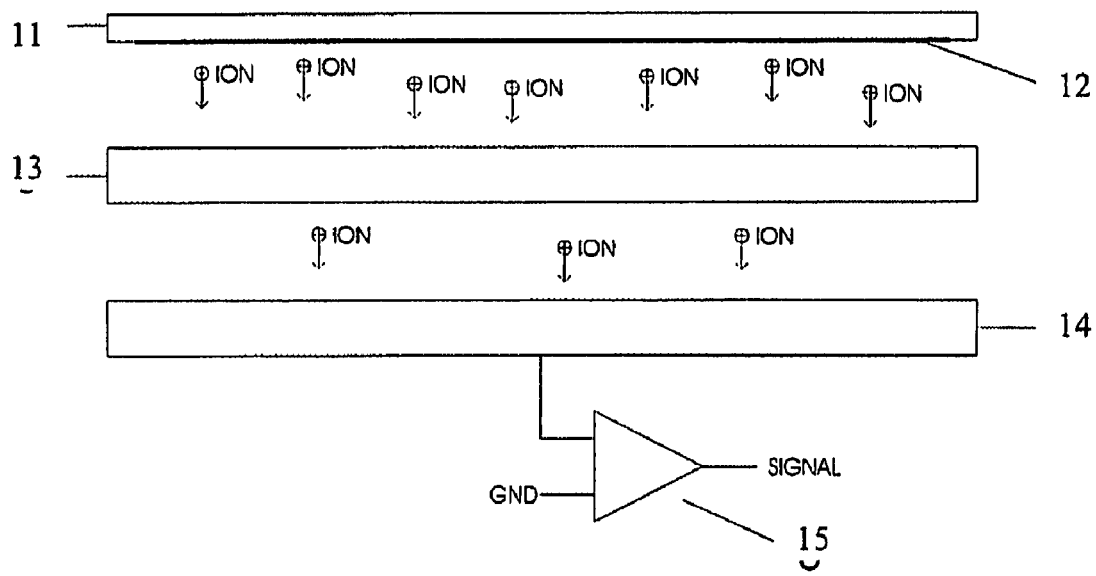
FIG. 6 is a schematic diagram of another embodiment of a spectrometer in accordance with the present invention.

An alternative spectrometer-arrangement is shown in FIGS. 6, 7, 8 and 9. This arrangement consists of an ionization source 12, a deflector electrode 11, a collector electrode 14, a current amplifier 15, and a tunable ion filter structure 13, as shown in FIG. 6. The ionization source is located on the deflector electrode, as with the structure of FIG. 3, while the filter structure 13 is here distinct from the collector electrode 14. The deflector electrode is held at a positive or negative voltage bias with respect to the collector electrode, so that ions created by the ionization source between the two are driven towards one of the electrodes. Ions directed towards the collector are selectively admitted the electrode by the tunable ion filter structure. Ions admitted to the collector are neutralized at the electrode surface and transfer their charge to the current amplifier, to produce an amplified signal for output. By tuning the filter structure, ions are permitted to pass depending on characteristic mobility value and are subsequently detected by the amplifier to produce an ion mobility spectrum signal.

Figure 7:
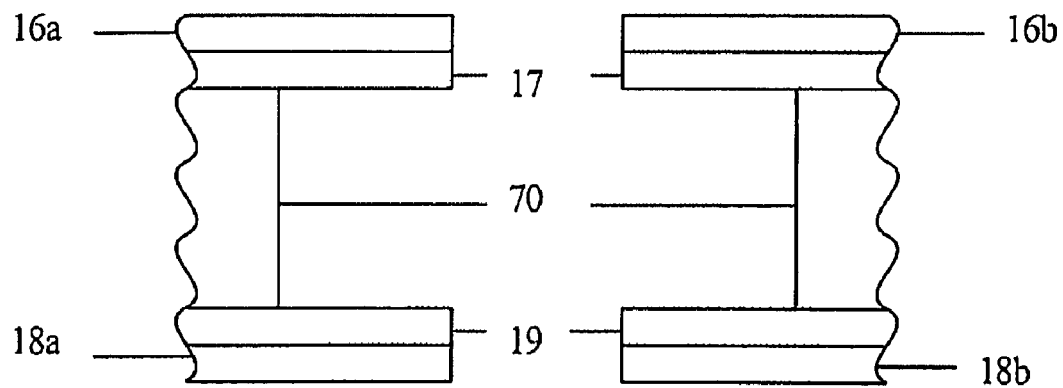
FIG. 7 shows the filter structure of the spectrometer of FIG. 6.
Figure 8:
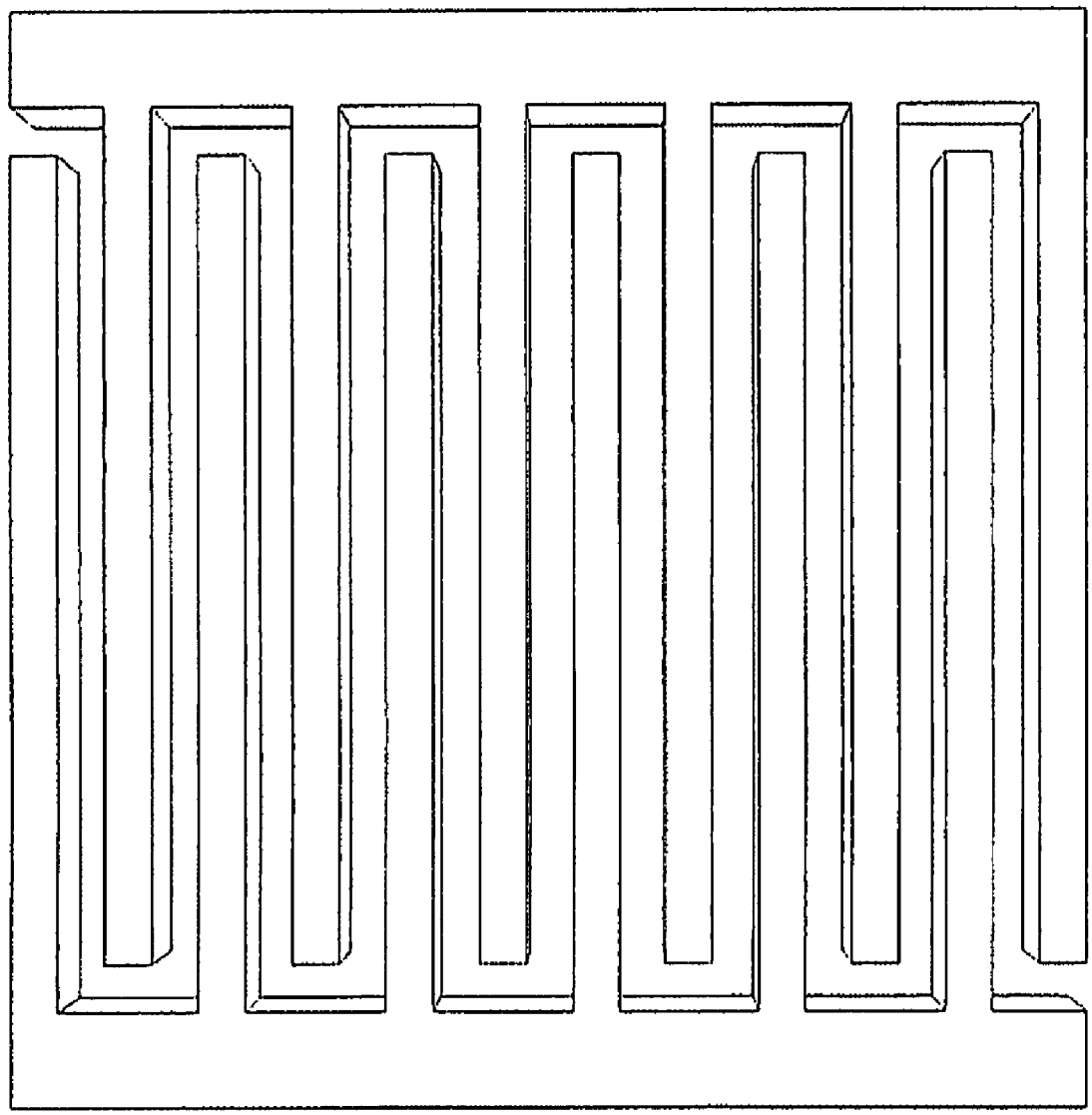
FIG. 8 shows an overhead view of the filter structure of FIG. 7.

The construction of the ion filter structure is shown in FIG. 7. In this embodiment, the structure consists of a conductive layer 16a, 16b on top of an insulative layer 17 on one side of a silicon wafer 70, and a conductive layer 18a, 18b on top of an insulative layer 19 on the opposite side. All layers may be on the order of several hundred nanometers thick. The conductive layers may be made of doped polysilicon and the insulative layers may be made of silicon nitride. The layers and silicon wafer are etched away to form the supported membrane structure shown. Each conductive layer is patterned as shown in FIG. 8, which is an overhead view of the filter (see also filter structure 50 of FIG. 2) to form two interdigitated electrodes. The insulative layers form a support membrane for structural rigidity. The silicon pillars between the membranes maintain a very precise fixed gap width and provide additional rigidity. In alternative embodiments, the electrodes may be curved or serpentine.

Figure 9A:
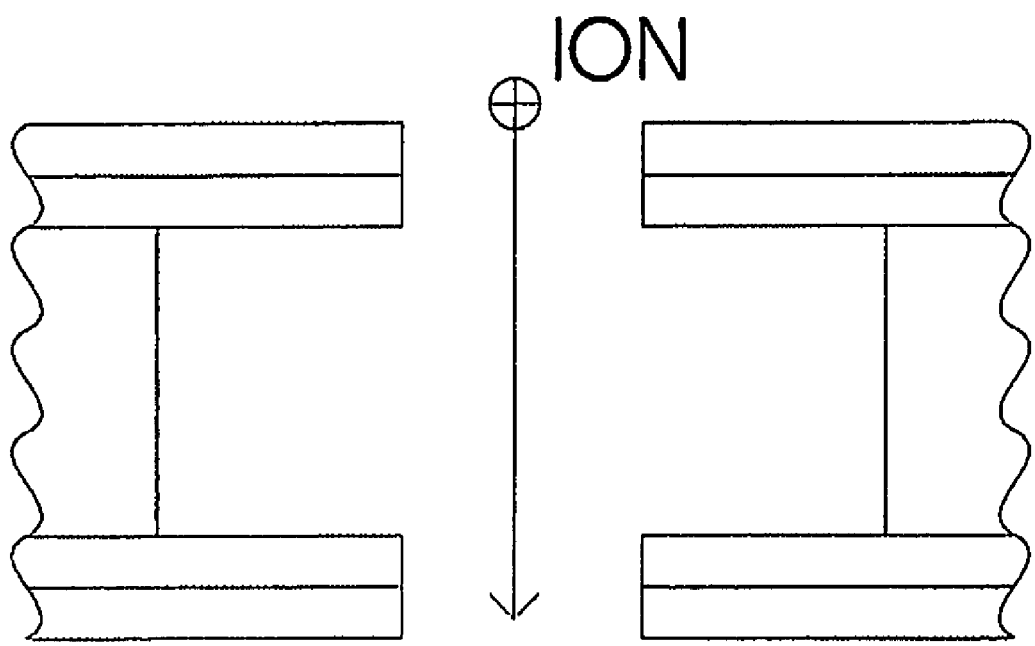
FIGS. 9a and 9b illustrate the operation of the filter structure of FIG. 7.
Figure 9B:
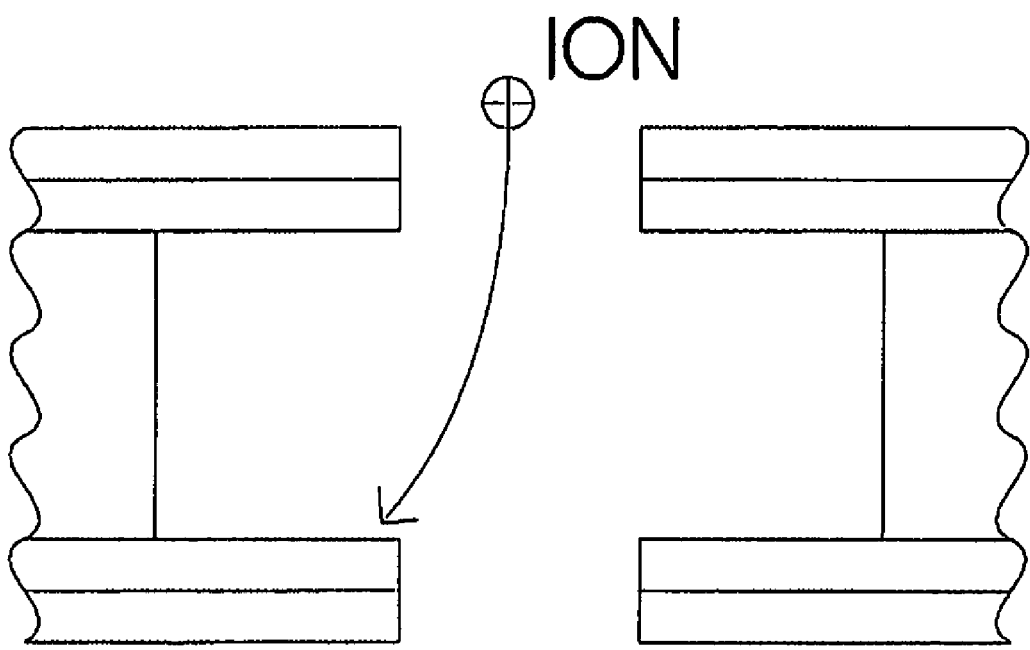

The action of the filter structure is depicted in FIG. 9. A square waveform is applied across each of the interdigitated structures such that one phase of the waveform has zero value, making the structures behave as Bradbury-Nielson gates. When the potential applied across the interdigitated features is zero, the electric field in the vicinity of the gate region is perpendicular to the membrane so that ions are directed through it (the gate is "open"). When the potential applied across the interdigitated features is non-zero, the electric field in the vicinity of the gate region is approximately parallel to the membrane so that ions are directed into one of the gate electrodes and therefore cannot traverse the membrane (the gate is "closed"). The zero value used for each gate is slightly different, so that an electric gradient exists between the gates when open and ions tend to be directed through the filter structure during this phase. Only ions moving quickly enough (with high enough mobility values) can make it through the filter structure for a particular waveform frequency. Ions with high enough velocities, and hence large mobility values, reach the collector electrode and are detected. Ions with velocities that are too slow, and hence mobility values too small, do not reach the collector. An ion mobility spectrum like that shown in FIG. 10 of the ambient gas is formed by scanning the frequency of the waveform and differentiating the signal output by the current amplifier.

In certain embodiments of the invention, the spectrometer may further comprise a membrane, and in particular a semi-permeable membrane. For example, the membrane may be made from expanded PTFE (such as that sold under the name GORE-TEX (RTM)), or from dimethylsilicone. Such semi-permeable membranes may find many uses in the invention.

The inlet of the spectrometer may be covered by a membrane. This has a number of functions; one is to prevent dust and particulates from entering the device, while the semi-permeable membrane still permits gaseous analytes to enter. The membrane may exclude polar molecules from the active region of the spectrometer; excessive polar molecules can lead to clustering which reduces resolution of the device and affects the data. The membrane serves to concentrate analytes in the region immediately adjacent the sensor, so improving sensitivity. Further, liquids may be passed over the membrane, such that the analyte can diffuse from the liquid into the device in gas phase, thereby permitting analysis of liquid samples. The membrane may incorporate a heating element; varying the temperature of the membrane can affect diffusion processes across the membrane so allowing additional selectivity.

Selection of appropriate membrane material may also be used to exclude particular molecular species from the device.

Figure 12:
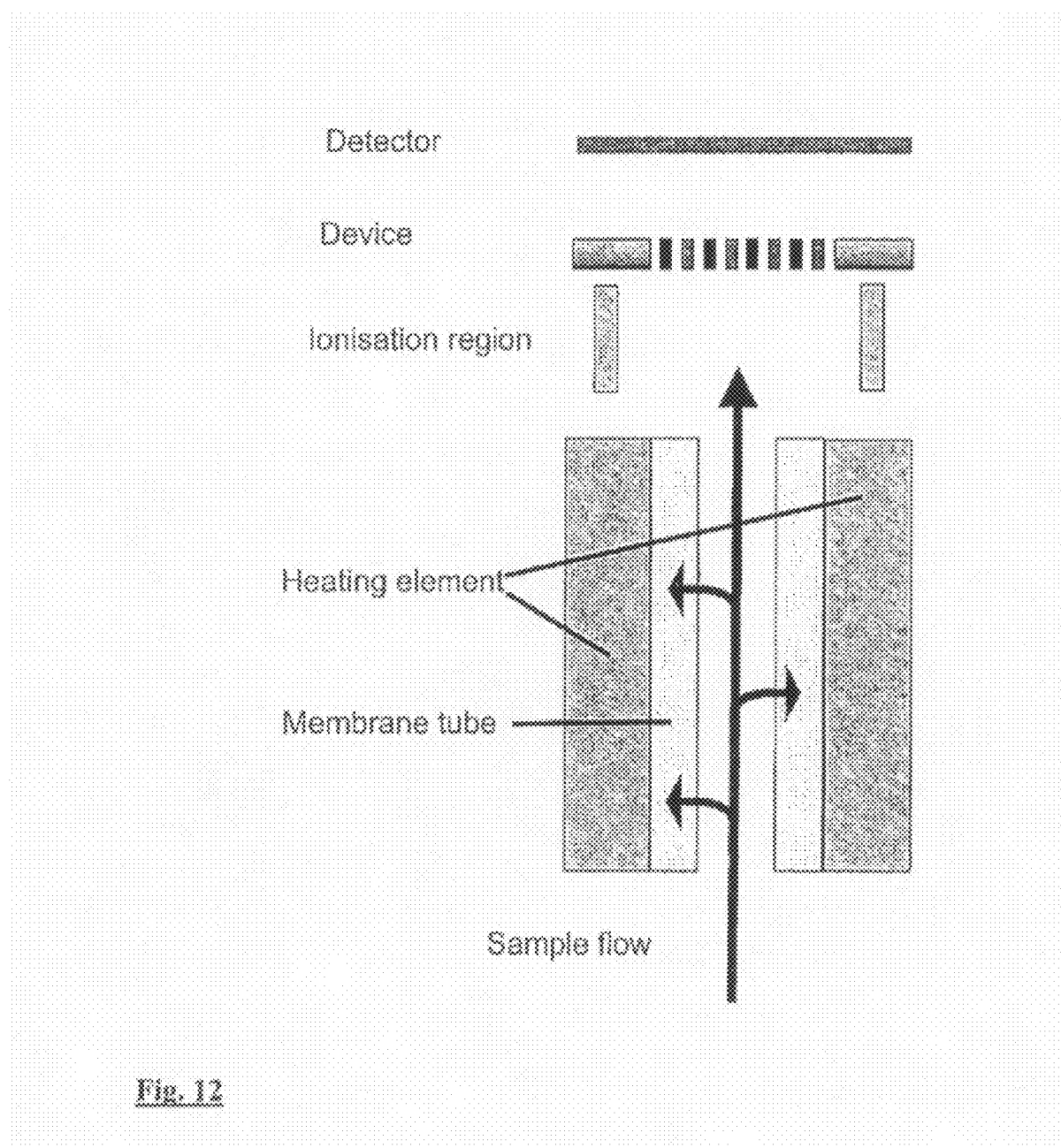
FIG. 12 shows the use of a heated membrane inlet tube with the present invention.
Figure 13:
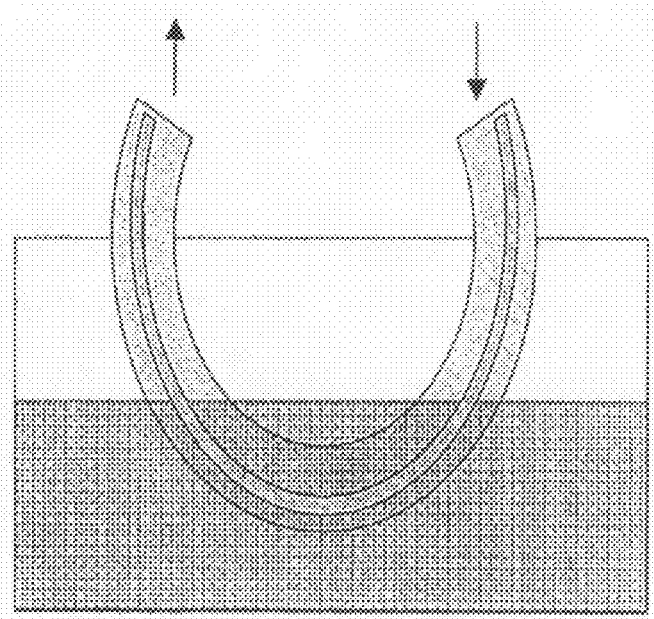
FIG. 13 shows the use of an inlet tube to sample fluids with the present invention.

A membrane may also be used as a pre-concentrator; particularly if the membrane also incorporates a heating element. Analytes may diffuse into the membrane where they will be held until the temperature is raised; this releases a relatively high concentration of analyte into the device. The membrane may simply cover the inlet of the spectrometer, but in preferred embodiments may take the form of an inlet tube leading to the device; sample may be continuously passed along the tube giving some sample data over time, while a concentrated plug of analyte may be released when desired from the inlet tube. For sampling liquids, an inlet tube may be immersed in the sample, allowing analyte to diffuse from the liquid into the membrane. Heating of the membrane releases analyte into the spectrometer. Examples of these are shown in FIGS. 12 and 13.

A separate membrane may also be used as a sample introduction device. A PDMS (polydimethylsilicone) membrane (or other suitable material) containing an embedded silicon wafer can be introduced into a liquid or gaseous sample. Analyte from the sample is adsorbed into the membrane. The sample introduction device is then located adjacent the spectrometer, and a current passed through the silicon wafer, serving to heat the wafer and hence the membrane. Adsorbed analyte is then desorbed adjacent the spectrometer. This arrangement allows sampling to take place at a location remote from the spectrometer. The sampling device may be connectable to the electronics of the spectrometer to permit current to be passed through the silicon wafer.

Figure 14:
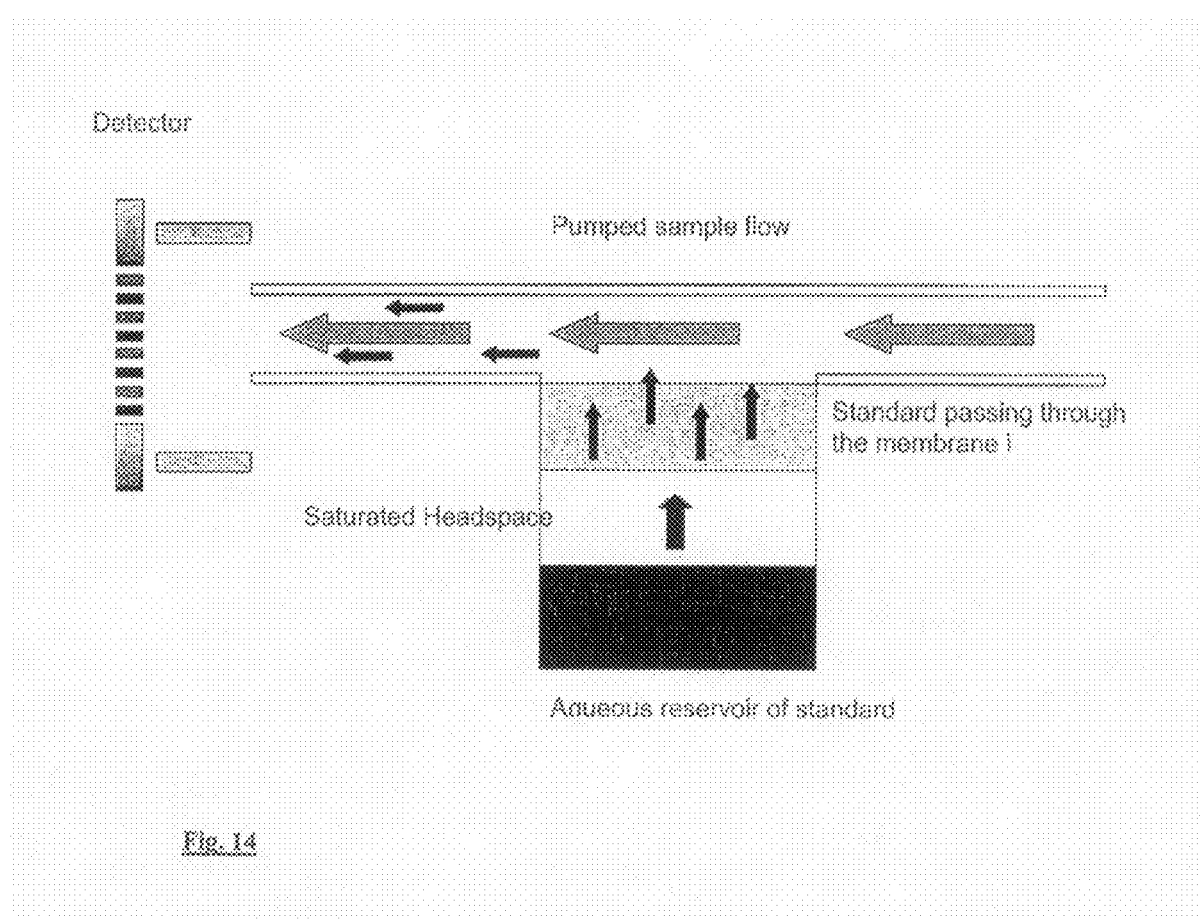
FIG. 14 shows the incorporation of a standard into the present invention.

Various membrane-related devices may be used to incorporate standards into the spectrometer. The use of standards can allow calibration of the spectrometer response, and in some circumstances can also correct for temperature or humidity variations. A membrane standard will release analyte at a generally constant rate dependent largely on the physical properties of the membrane chosen, rather than on the concentration of the standard itself. Such standards are therefore relatively simple to manufacture, robust, and can be recharged without requiring accurate recalibration. Loading of the membrane standards may be achieved in numerous ways. For solids, the standards may be introduced during the membrane curing process. For liquids or gases the membrane may be used to enclose a sample of the standard; and for gases the membrane can be impregnated and stored in a controlled headspace. The membrane standard may be a separate component from the spectrometer, or may be incorporated internally into the spectrometer to allow ready calibration; for example, a standard may be connected to an inlet pipe leading to the spectrometer; this is illustrated in FIG. 14. An internal standard may also be used for continual monitoring and validation of sampling data. The standards used will depend on the particular application, but preferred standards will have a high proton/electron affinity or can donate protons/electrons; can be separated from target compounds; and will not be masked by naturally occurring interferents.

Multiple filters and/or detectors may be combined in a detector array to improve sensitivity to a range of analytes. With a single filter, it is necessary to sweep the compensation voltage to tune the filter to transmit certain ion species; for a large proportion of the time the compensation voltage may not be tuned to the analyte of interest, and there is a delay time as the voltage is swept. Combination of several filters and/or detectors allows each filter to remain tuned to a single voltage to detect a specific analyte of interest, while the array format allows detection of a range of different analytes. The output from the sensor array would be a discrete spectrum with a number of channels, corresponding to the number of analytes of interest. It is also possible to have several filters tuned to the same voltage but with different dopant chemistries in each device to improve screening and reduce interference effects; or even several identical filters for redundancy.

Figure 15:
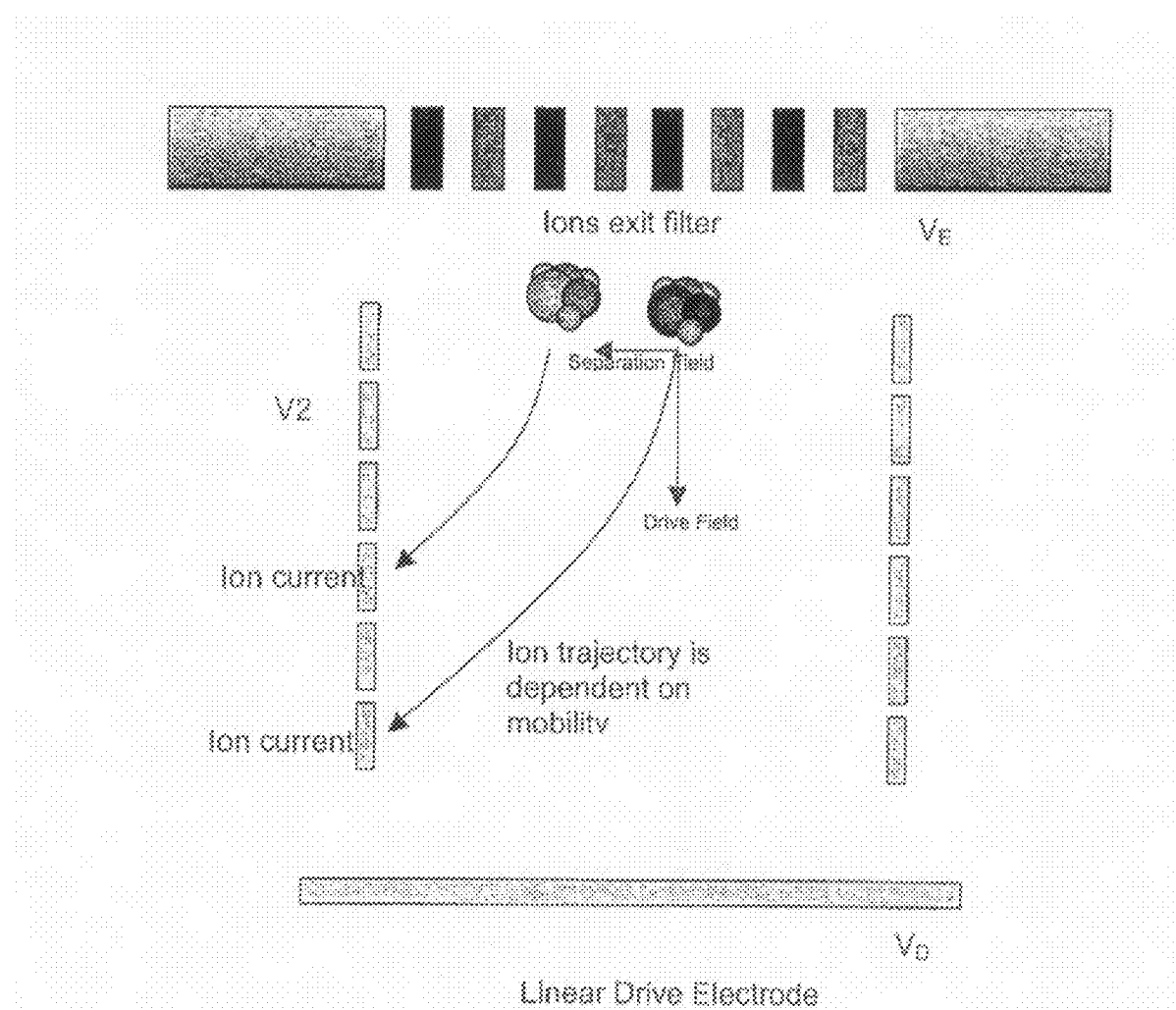
FIG. 15 shows a detector electrode array as may be used with the present invention.

Further improvements in sensitivity can be achieved by using multiple detector electrodes with a single filter. When a single detector electrode is used, this is a single plate which measures the total ion current which may contain several ion types, while only a single type may be of interest. A series of discrete detector electrodes may be used, orthogonal to the exit path taken by the ions as they leave the filter; this creates an orthogonal field drawing the ions toward the detectors. The speed at which the ions move toward the electrodes is dependent upon the mobility of the ion; and as there is still a linear component to the electric field, ions of differing mobilities will strike different detector electrodes. This permits greater sensitivity in detecting different ion species which pass the filter. An example detector electrode array is shown in FIG. 15.

Figure 16:
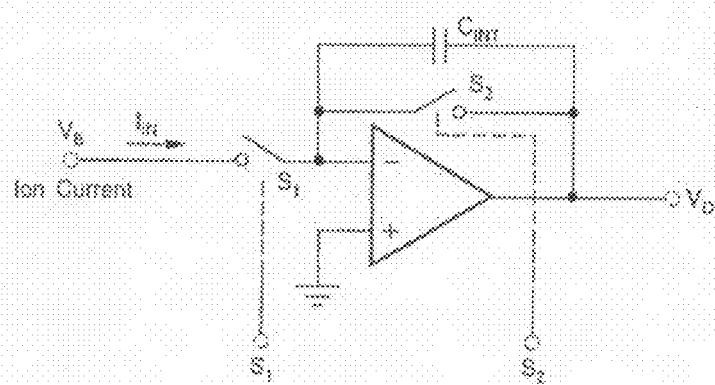
FIG. 16 shows a switched integrator as may be used with embodiments of the present invention.

Another means whereby detector sensitivity may be improved is by coupling the detector electrode to a capacitor which gradually builds up charge as individual ions strike the detector plate. Periodic discharge of the capacitor allows the ion contributions to be summed over time, thereby increasing sensitivity and signal to noise ratio of the device. A switched integrator may also or instead be used to improve sensitivity in certain circumstances. The ion detector is connected by a switch to an integrator; this is switched to measure output voltage, and a second switch is cycled to reset the device. An example is shown in FIG. 16.

In certain embodiments, the spectrometer of the present invention may be operated in a switch mode for detection; that is, the detector is activated periodically to take a sample at regular intervals. This operating mode may be used to moderate power consumption and to prolong operating life of the device. This is particularly of benefit when a device is intended to be used for prolonged monitoring of a sample; for example, in security applications or the like.

Operation of the spectrometer could also include varying the temperature and/or pressure at which the device is run, to vary the performance of the device.

Although the invention thus far has been described in terms of using only an electric field to drive ions through the filter, it will be apparent that it is possible to use the filter in combination with a gas flow, either a counterflow as previously described, or as a flow in the same direction as the ion flow driven by the electric field.

A gas flow may be used in embodiments solely for introduction of ions into the spectrometer, while the electric field operates once the ions have entered the device. Alternatively, the filter may be operated with only a transverse electric field to selectively admit ions; longitudinal movement of the ions is controlled purely by a longitudinal gas flow.

In some embodiments of the invention, the filter structure may be fabricated as completely solid metal elements, for operating in gas flow mode, or as a metal coated silicon or other wafer structure. Metal coating may be formed by, for example, sputtering, evaporation, electroplating, electroless electroplating, atomic layer deposition, or chemical vapour deposition. A solid metal device may be produced by water cutting, laser cutting, machining, milling, or LIGA. Although this arrangement does not have the advantages of a purely electric field driven device, the ability to make use of a miniaturised filter with a gas flow propulsion has advantages such as reducing the operating voltage. Use of an interdigitated array of ion channels compensates to some extent for the lower voltage used.

As mentioned above, gas flow may be used to couple ions into the spectrometer. An alternative introduction method is to use electrospray ionisation. An analyte dissolved in solvent is forced through a capillary thin needle point which is charged. This induces a charge on the expelled droplets which are accelerated towards an oppositely charged pinhole orifice. This allows the use of a non-radioactive ionizer, as well as permitting liquid phase ionisation without heating, which could degrade some analytes, and also permits the ionisation of some macromolecules such as peptides.

Figure 17:
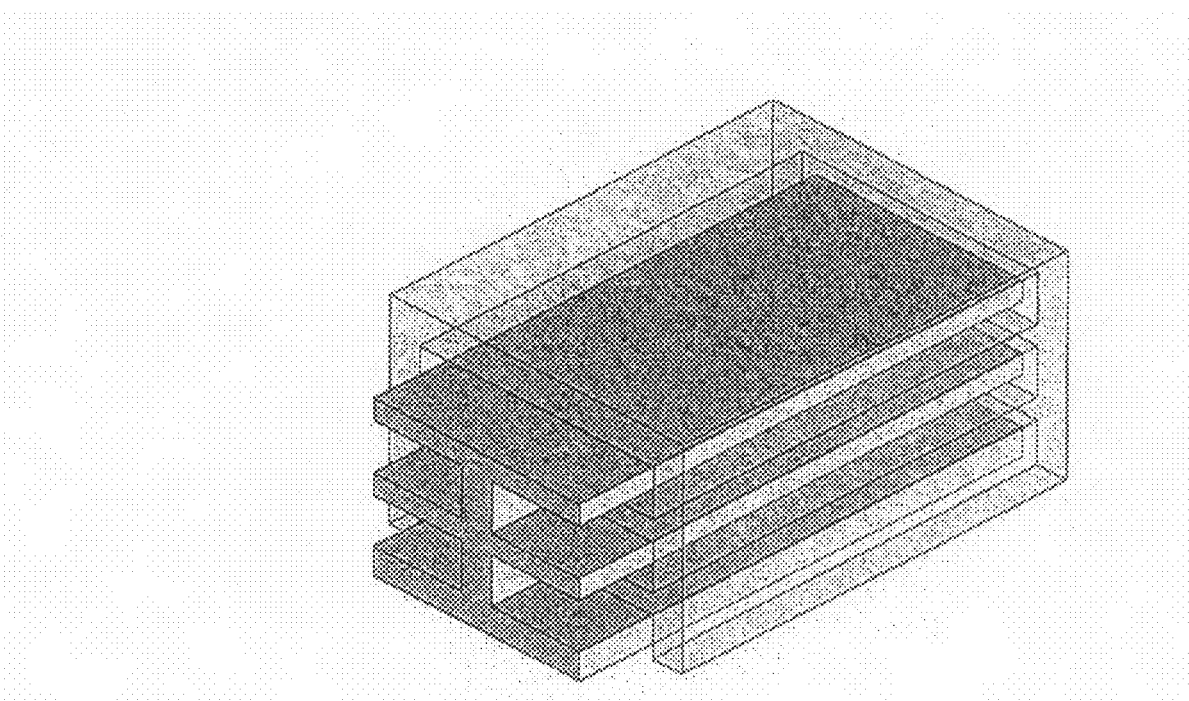
FIG. 17 shows a schematic illustration of a filter structure formed from multiple planar stacked layers.

While the filter structure of the present invention has been described primarily in terms of having a wafer structure, it will be apparent that suitable filter structures may be made from multiple stacked planar layers, to provide a filter having much longer ion channels than those of a wafer structure. Alternate layers of the stack may be electrically connected in parallel. While a wafer structure is particularly suited to microscale manufacture, a stacked planar arrangement may be achieved using macro scale components, such as metal coated ceramic layers, as well as microscale such as using the EFAB process. Due to the increase in length of ion channels in this embodiment, it is preferable that this embodiment of the invention operates with a combination of gas flow and electric field to drive ions through the channels. A schematic illustration of this structure is shown in FIG. 17.

The filter structure of the present invention may be driven differentially; that is, the AC component of the transverse field may be applied to opposing sides of the ion channel out of phase.

The ion channel may further comprise inert conductive particles located on the walls thereof; these may be nanoparticles, for example gold nanoparticles. Where the ion channel comprises silicon, over time some oxidation of the surface will occur, altering the electrical properties of the device. The inert particles will not be subject to oxidation, and so will provide a conductive surface for ion contact despite oxidation of the surface of the channel.

The spectrometer of the present invention may be coupled to one or more other detection or analysis devices; or the spectrometer may be operated in combination with one or more other analysis techniques. The spectrometer may receive analytes from such a device, or may transfer analytes to said device. Representative additional detection or analysis techniques include mass spectroscopy, gas chromatography, ion mobility spectroscopy, liquid chromatography, capillary electrophoresis, flame ionization detection, thermal conductivity detection, and solid phase microextraction. Any or all of these may be combined with the present invention, and spectrometers of the present invention may also be combined with other spectrometers according to the invention.

Two representative uses of spectrometers of the present invention include drug breath analysis, and quality control of wine. For drug breath analysis, the device may be used to detect volatile metabolites originating from the use of a controlled substance in the exhalations of a subject. This would be much quicker and simpler than existing analysis techniques which generally rely on hair, blood, or urine analysis. The metabolites to be detected depend on the substance to be screened for.

Wine is susceptible to taint or corking which impairs the taste and quality of the drink. Corked wine includes a number of contaminants such as tri- and tetra-chloroanisoles, and tri- and tetra-chlorophenols. Spectrometers of the present invention may be used to detect these compounds. In some embodiments, a spectrometer may be integrated into a cork-shaped housing intended to sit within the neck of a standard wine bottle, allowing for ready testing of wine samples. A simple red or green light alert may be incorporated into the device to allow rapid reading of results. Alternatively, the device may be incorporated into a wine bottling production line to ensure quality control of the bottling. The device may also be used to sample air drawn over corks before bottling occurs, to check for contaminants in the corks themselves.

The invention claimed is:

1. A field asymmetric ion mobility spectrometer comprising an ionizer, an ion filter, a deflector electrode, an ion detector, and a controller;
   wherein the ion filter is located between the deflector electrode and the ion detector and defines at least one ion channel along which ions may pass from the ionizer to the ion detector;
   wherein the ion channel is defined by a plurality of conductive layers separated along the length of the channel by at least one non-conductive layer; and
   wherein the controller is configured to apply an oscillating electric potential having a first phase and a second phase to the conductive layers of the ion channel, the electric potential directing ions within the ion channel toward the ion detector in the first phase and in a direction other than toward the ion detector in the second phase.

2. The spectrometer of claim 1, wherein the deflector electrode deflects ions away from the ionizer and toward the ion detector.

3. The spectrometer of claim 1, wherein the controller allows the application of a time-varying electric potential to the conductive layers.

4. The spectrometer of claim 3, wherein the electric potential is time-varying in an asymmetric manner.

5. The spectrometer of claim 1, wherein the controller allows the electric potential to be selectively varied.

6. The spectrometer of claim 1, wherein the filter comprises a plurality of ion channels.

7. The spectrometer of claim 6, wherein the conductive layers form electrodes and the ion channels are defined at either end by apertures in said electrodes.

8. The spectrometer of claim 1, wherein the filter comprises two or more interdigitated electrode arrays, each array having a plurality of channel-defining slots.

9. The spectrometer of claim 1, wherein the filter comprises a resistive or semiconductive substrate on which the conductive layers and non-conductive layer are provided.

10. The spectrometer of claim 9, wherein the substrate is the ion detector.

11. The spectrometer of claim 1, wherein two conductive layers are provided.

12. The spectrometer of claim 1, wherein two non-conductive layers are provided.

13. The spectrometer of claim 1, wherein the filter has a structure C-NC-C-NC, where C and NC represent conductive and non-conductive layers respectively.

14. The spectrometer of claim 13, wherein the filter further includes a substrate.

15. The spectrometer of claim 1, wherein the filter has a structure C-NC-substrate-NC-C, where C and NC represent conductive and non-conductive layers respectively.

16. The spectrometer of claim 1, wherein the spectrometer comprises a plurality of functional layers.

17. The spectrometer of claim 1 further comprising a semipermeable membrane.

18. The spectrometer of claim 17, wherein the membrane comprises a heating element.

19. The spectrometer of claim 17, wherein the membrane is in the form of an inlet tube.

20. The spectrometer of claim 1 that comprises a standard.

21. The spectrometer of claim 1 that comprises multiple ion filters.

22. The spectrometer of claim 1 that comprises multiple ion detectors.

23. The spectrometer of claim 1, further comprising a gas flow generator that can generate a gas flow through the spectrometer.

24. The spectrometer of claim 23, wherein the gas flow is a counterflow against the direction of movement of ions.

25. The spectrometer of claim 1, further comprising a heater configured to heat the filter.

26. The spectrometer of claim 25, wherein the heater comprises a substrate which is heated by Joule-effect heating.

27. The spectrometer of claim 1, wherein the ion channel includes inert conductive particles located on the walls of the channel along its length.

28. The spectrometer of claim 1, wherein the ion filter comprises a wafer-like form.

29. The spectrometer of claim 1, wherein the ion filter comprises a plurality of stacked planar layers.

30. The spectrometer of claim 1, wherein the ion channel is curved or serpentine.

31. The spectrometer of claim 1 that is coupled to one or more other detection or analysis devices.

32. The spectrometer of claim 1, further comprising a controller configured to operate the spectrometer periodically to sample at intervals.

33. The spectrometer of claim 1, wherein the ion detector comprises an electrode coupled to a capacitor that is periodically discharged.

34. A method of analyzing a sample, the method comprising:
   ionizing a sample to generate ions adjacent an ion channel within the field asymmetric ion mobility spectrometer of claim 1;
   biasing the ions such that, in the absence of other forces, they travel along the ion channel;
   applying an oscillating electric potential to the conductive layers, such that an electric field is established within the ion channel; and
   detecting generated ions that have passed through the ion channel.

35. An ion filter for use in a field asymmetric ion mobility spectrometer, the filter defining at least one ion channel along which ions may pass, wherein the ion channel is defined by a plurality of conductive layers separated along the length of the channel by at least one non-conductive layer.

36. The filter of claim 35, having a structure C-NC-C-NC, where C and NC represent conductive and non-conductive layers respectively.

37. The filter of claim 35, having a structure C-NC-substrate-NC-C, where C and NC represent conductive and non-conductive layers respectively.

38. A method of manufacturing a field asymmetric ion mobility spectrometer, the method comprising:
   providing a generally planar resistive substrate having thereon a plurality of conductive layers separated by at least one non-conductive layer;
   patterning the substrate to provide a filter comprising two or more interdigitated electrode arrays defining a plurality of ion channels themselves defined by a plurality of conductive layers separated along the length of the channel by at least one non-conductive layer; and
   attaching said filter on one face to a generally planar ionization layer comprising means for ionizing an analyte.

39. An ion filter for use in a spectrometer such as a field asymmetric ion mobility spectrometer, the filter comprising a pair of interdigitated electrodes defining a plurality of ion channels along which ions may pass.

40. The spectrometer of claim 1, wherein the direction other than toward the ion detector is a direction away from the ion detector.

41. The spectrometer of claim 1, wherein the direction other than toward the ion detector is a direction toward at least one of said conductive layers.

42. The method of claim 34, wherein the direction other than toward the ion detector is a direction away from the ion detector.

43. The method of claim 34, wherein the direction other than toward the ion detector is a direction toward at least one of said conductive layers.

* * * * *

UNITED STATES PATENT AND TRADEMARK OFFICE
CERTIFICATE OF CORRECTION

| | |
|---|---|
| PATENT NO. | : 7,498,570 B2 |
| APPLICATION NO. | : 10/571871 |
| DATED | : March 3, 2009 |
| INVENTOR(S) | : Paul Boyle et al. |

It is certified that error appears in the above-identified patent and that said Letters Patent is hereby corrected as shown below:

On the title page item (73) Assignee:
delete "Owistone" and replace with --Owlstone--.

Signed and Sealed this

Twenty-third Day of June, 2009

JOHN DOLL
*Acting Director of the United States Patent and Trademark Office*